United States Patent
Monson et al.

(10) Patent No.: US 7,988,678 B2
(45) Date of Patent: Aug. 2, 2011

(54) NEEDLE MOUNTING ASSEMBLY FOR A MEDICATION INJECTION DEVICE

(75) Inventors: Rodney Hal Monson, Wauksgan, IL (US); Travis Schultz Lee, Chicago, IL (US); Kenneth Alan Ritsher, Chicago, IL (US)

(73) Assignee: Eli Lilly and Company, Indianapolis, IN (US)

( * ) Notice: Subject to any disclaimer, the term of this patent is extended or adjusted under 35 U.S.C. 154(b) by 202 days.

(21) Appl. No.: 12/307,702

(22) PCT Filed: Jul. 6, 2007

(86) PCT No.: PCT/US2007/072893
§ 371 (c)(1),
(2), (4) Date: Jan. 6, 2009

(87) PCT Pub. No.: WO2008/008694
PCT Pub. Date: Jan. 17, 2008

(65) Prior Publication Data
US 2009/0312715 A1    Dec. 17, 2009

Related U.S. Application Data

(60) Provisional application No. 60/807,002, filed on Jul. 11, 2006.

(51) Int. Cl.
*A61M 5/31* (2006.01)
(52) U.S. Cl. ........ 604/240; 604/200; 604/201; 604/241; 604/243
(58) Field of Classification Search .......... 604/200, 604/201, 205, 206, 239, 240, 241, 242, 243, 604/244
See application file for complete search history.

(56) References Cited

U.S. PATENT DOCUMENTS

| | | |
|---|---|---|
| 2,834,346 A | 5/1958 | Adams |
| 3,895,633 A | 7/1975 | Bartner et al. |
| 3,916,893 A | 11/1975 | De Felice |
| 4,568,336 A | 2/1986 | Cooper |
| 4,624,393 A | 11/1986 | Lopez |
| 4,950,241 A | 8/1990 | Ranford |
| 5,002,537 A | 3/1991 | Hoffman et al. |
| 5,047,016 A | 9/1991 | Dolgin et al. |
| 5,205,833 A | 4/1993 | Harsh et al. |
| 5,445,620 A | 8/1995 | Haber et al. |

(Continued)

FOREIGN PATENT DOCUMENTS

GB    2 420 713    6/2006

(Continued)

*Primary Examiner* — Bhisma Mehta
(74) *Attorney, Agent, or Firm* — Edward J. Prein

(57) ABSTRACT

A needle mounting assembly for mounting a pen needle in fluid communication with a medication cartridge. A collet defines an opening in which is slidably fittable the outlet end of the cartridge. The collet is shiftable relative to the cartridge outlet end. When the collet is disposed in a first axial position, a plurality of fingers of the collet extend forward of the cartridge outlet end and are disposed in a first radial arrangement in which a needle hub of the pen needle can be freely axially placed onto and freely axially removed from the plurality of fingers. When the collet is moved to a second position, the plurality of fingers are shifted by engagement with the cartridge outlet end to operationally secure the needle hub. When the collet is moved back to the first position, the plurality of fingers shift back for free axial removal of the needle hub from the mounting assembly.

7 Claims, 5 Drawing Sheets

U.S. PATENT DOCUMENTS

| | | |
|---|---|---|
| 5,480,390 A | 1/1996 | Hajishoreh |
| 5,554,134 A | 9/1996 | Bonnichsen |
| 5,611,786 A | 3/1997 | Kirchhofer et al. |
| 5,637,101 A | 6/1997 | Shillington |
| 5,693,027 A | 12/1997 | Hansen et al. |
| 5,693,028 A * | 12/1997 | Shillington ............ 604/240 |
| 5,968,021 A | 10/1999 | Ejlersen |
| 6,017,331 A | 1/2000 | Watts et al. |
| 6,126,646 A | 10/2000 | Hansen et al. |
| 6,497,684 B2 | 12/2002 | Witowski |
| 6,969,374 B2 | 11/2005 | Krantz et al. |
| 2003/0144633 A1 | 7/2003 | Kirchhofer |

FOREIGN PATENT DOCUMENTS

| | | |
|---|---|---|
| WO | WO 03/047667 A1 | 6/2003 |
| WO | WO 2004/004812 | 1/2004 |
| WO | WO 2004/047894 A1 | 6/2004 |
| WO | WO 2004/047895 A1 | 6/2004 |

* cited by examiner

US 7,988,678 B2

1

NEEDLE MOUNTING ASSEMBLY FOR A MEDICATION INJECTION DEVICE

This is the national phase application, under 35 USC 371, for PCT/US2007/072,893, filed 6, Jul. 2007, which claims the benefit, under 35 USC 119(d), of US provisional application No. 60/807,002 filed 11, Jul. 2006.

BACKGROUND OF THE INVENTION

The present invention pertains to medication injection devices, and, in particular, to mounting injection needles thereon.

A wide variety of medication injection devices are available which allow people, such as patients or health care professionals, to administer pharmaceuticals to themselves or others. One class of injection devices broadly known as pen injectors uses a type of injection needle known as a pen needle, which pen needle may be removed and disposed of after a single use, with an identical replacement pen needle to be mounted to the pen injector when used later. Most pen needles have a threaded hub that can be screwed onto and off of the pen injector. Another known pen needle disclosed in U.S. Pat. No. 5,611,786 can be axially forced onto a pen injector for use, and can be screwed off, or pulled off forcefully, from the pen injector for disposal. While not overly problematic for many users, manipulating or forcing the pen needles in these ways may be difficult or inconvenient for some people.

Thus, it would be desirable to provide an improved needle mounting assembly that provides one or more advantages over the prior art.

BRIEF SUMMARY OF THE INVENTION

In one form thereof, the present invention provides a needle mounting assembly for mounting a pen needle in fluid communication with a medication cartridge including an outlet end with a septum. The needle mounting assembly includes a collet and a stop collar. The collet defines an opening in which is slidably fittable the outlet end of the cartridge, and the collet is shiftable relative to the cartridge outlet end between a first axial position and a second axial position. The collet includes a base and a plurality of fingers that are forward of the base. The stop collar is one of axially secured to and integrally formed with one of the cartridge and a retainer for the cartridge. The stop collar is adapted to halt movement of the collet at the first axial position when the collet moves from the second axial position. When the collet is disposed in the first axial position, the plurality of resilient fingers extend forward of the cartridge outlet end and are disposed in a first radial arrangement in which a needle hub of the pen needle can be freely axially placed onto and freely axially removed from the plurality of resilient fingers. When the collet is moved to the second position from the first position when the needle hub is freely placed onto the plurality of resilient fingers, the plurality of resilient fingers are shifted by engagement with the cartridge outlet end to a second radial arrangement to operationally secure the needle hub for medication delivery with a tip of a cannula of the pen needle piercing the cartridge septum. When the collet at the second position with the needle hub operationally secured by the plurality of outlet fingers is moved to the first position, the tip of the cannula of the pen needle is withdrawn from the cartridge septum and the plurality of resilient fingers shift back to the first radial arrangement for free axial removal of the needle hub from the mounting assembly.

2

One advantage of the present invention is that a needle mounting assembly may be provided which allows mounting and dismounting of a pen needle in an easy and intuitive manner.

Another advantage of the present invention is that a needle mounting assembly may be provided which allows mounting and dismounting of a standard pen needle having an internally threaded hub without any twisting or turning of that pen needle.

Yet another advantage of the present invention is that a needle mounting assembly may be provided which allows dismounting of a standard pen needle after use without a user touching the used pen needle.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
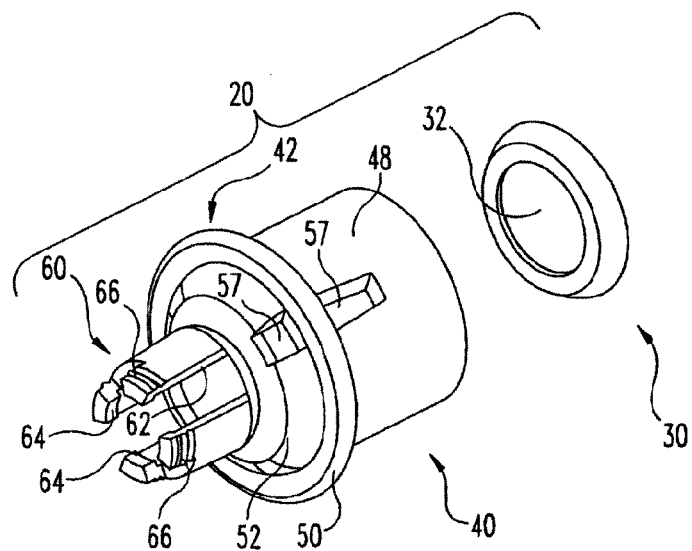
FIG. 1 is a perspective view in exploded form of a first embodiment of a needle mounting assembly of the present invention.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

Figure 2:
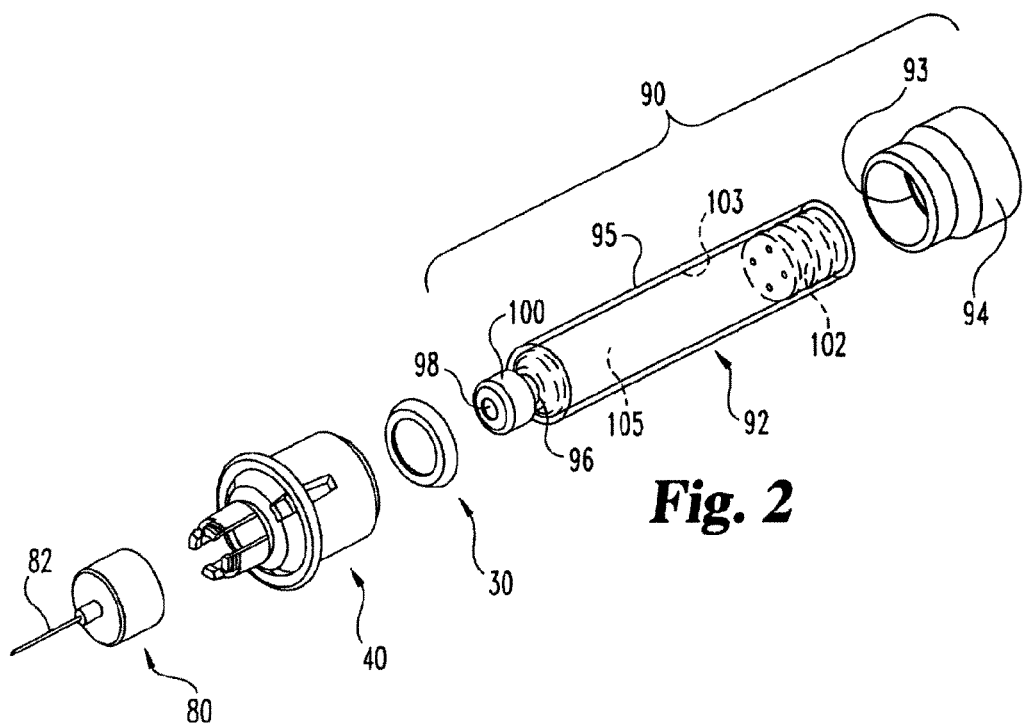
FIG. 2 is a perspective view in exploded form of the needle mounting assembly of FIG. 1 with a pen needle and cartridge assembly.

Referring now to FIG. 1, there is shown a first embodiment of a needle mounting assembly of the present invention. This embodiment permits a pen needle to be mounted in fluid communication with a medication cartridge in a convenient manner, and then to be dismounted or removed from that cartridge without the user having to grip or even touch the pen needle. This needle mounting assembly, generally designated 20, includes a stop collar 30 and a pen needle-engaging collet 40. While assembly 20 in FIG. 2 is shown used with a medication cartridge assembly that includes a feature allowing direct attachment to an injection device, assemblies of the present invention may be used with an injection device retainer that removably mounts a standard cartridge.

Figure 4:
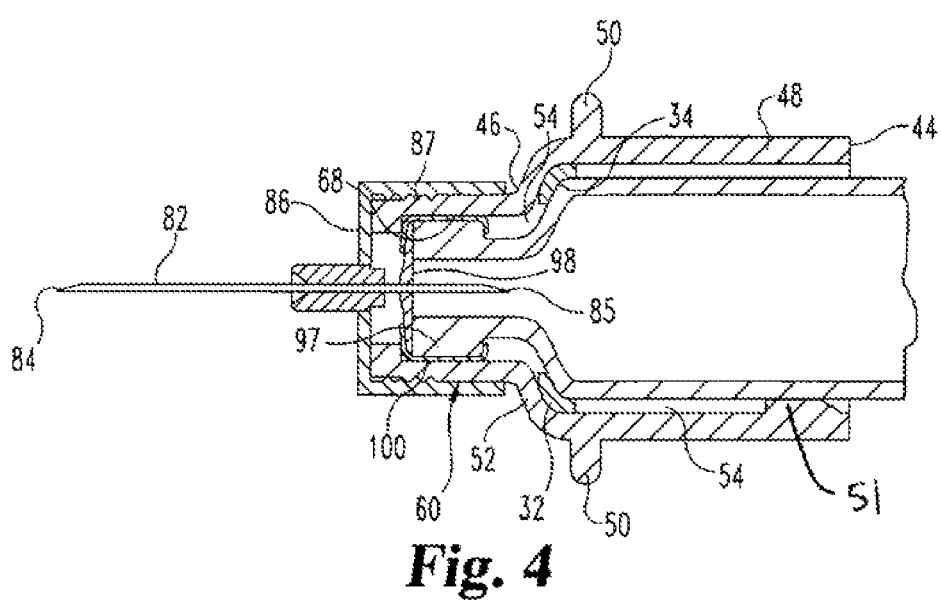
FIG. 4 is a longitudinal cross-sectional view of the forward portion of FIG. 3 taken along line 4-4.

Stop collar 30 interacts with collet 40 to prevent collet 40 from being inadvertently removed from a medication cartridge with which it is associated during pen needle removal described below, and further aids in radially centering the collet. Collar 30 is formed in one piece of a suitably durable material, such as pc/abs plastic or polypropylene, in a complete or continuous ring shape that defines a central opening 32 into which axially inserts the forward end of a known medication cartridge, shown in FIG. 2 at 92, during manufacturing assembly of mounting assembly 20. Collar 30 is sized and has an interior surface 34 shown in FIG. 4 contoured to fit the cartridge body where it transitions from a cylindrical barrel 95 to a stepped down neck portion 96. Collar 30 is axially and rotationally secured to the cartridge body, such as with adhesives or press fit. In a situation where the cartridge body includes a glass tube encased within a protective plastic sleeve, the collar may mount directly to or be integral with such protective sleeve.

Collar 30 is particularly adapted for use with collet 40 that is axially shiftably mountable thereon. Different stop collars, including those having different shapes and axial positionings, may be employed within the scope of the invention. By way of example, a stop collar need not be a continuous ring that is secured as a single piece to a cartridge or retainer, but rather may be formed of one or more angularly spaced, protruding ribs integrally formed with or separately secured to the medication cartridge or retainer.

Collet 40 is made in one piece of a durable material having sufficient resiliency to allow repeated splaying and return of its needle hub-engaging fingers described below. Suitable materials include, for example, molded plastics, metals or composites. With additional reference to FIG. 4, collet 40 includes a base 42 extending from a rearward end 44 to a forward end 46. Base 42 includes a cylindrical sleeve 48, a push rib 50 that completely encircles the outer periphery of sleeve 48 at a forward region thereof, and a tapering sleeve portion 52 forward of rib 50. The interior surface of sleeve 48 includes at least one detent, such as a plurality of detents, such as two, three, or more angularly spaced detents 51, that jut radially inward. Each detent includes a radially extending forward end for engagement with collar 30, and a ramped rearward end that aids the detent in sliding over the collar to a snap fit arrangement during initial assembly. Collet 40 also includes a plurality of pen needle-engaging fingers or tabs, generally designated 60, that project forward from sleeve portion 52 at the forward end 46 of the collet base. Collet 40 includes an interior opening or hole 54 axially extending therethrough that is sized and shaped to accommodate the forward portion of cartridge 92. Openings 57 located forward and rearward of push rib 50 facilitate injection molding of the component.

Fingers 60 are four in number and arranged in a circular pattern, each evenly angularly spaced from the adjacent fingers. Fingers 60 are constructed such that when in a relaxed or neutral state, the fingers in the forward direction tilt radially inward, resulting in the forward region of the fingers occupying a smaller circular profile than the rearward region of the fingers. Different numbers of fingers, including two or three, may be used instead of the four shown so long as a satisfactory gripping of the pen needle hub is realized thereby. Each finger 60 has a generally slat-shaped body 62 with a radially inward protruding lip 64 at its forward end. The outer radial periphery of each finger body includes thread sections 66, which threads are segments of a common threading of all the fingers. This threading is complementary to the internal threading of standard pen needle hubs for engagement therewith. The outer radial periphery alternatively possibly may be equipped with teeth, posts or ribs that engage the internal threading, or with barbs made of a harder material that dig into the hub interior, or with resilient material that absorbs dimensional variations to promote a solid engagement with the pen needle. The inner radial periphery of each finger body has a smooth surface 68 that serves as a cammable surface when the cartridge forward end is forced forward relative to collet 40 during pen needle mounting.

Needle mounting assembly 20 is shown in the exploded view of FIG. 2 with a pen needle 80 and a cartridge assembly 90, neither of which components form a part of the present invention.

Cartridge assembly 90 includes a cartridge of known construction, generally designated 92, and a fastening sleeve 94. Cartridge 92 includes a tubular body made of glass having a barrel portion 95, and a reduced-diameter neck portion 96 at the forward end of barrel portion 95. The cartridge also includes a needle-pierceable septum 98 that is secured in a fluid-tight manner over the forward, outlet end of the cartridge body by an apertured aluminum cap or crimp seal 100 that is crimped over a radially enlarged forward end 97 of the neck portion 96. A sealing piston 102 is axially slidably and sealably engaged with the barrel interior wall 103 and serves to define the rearward end of the medication filled, variable volume reservoir 105 of the cartridge.

Figure 3:
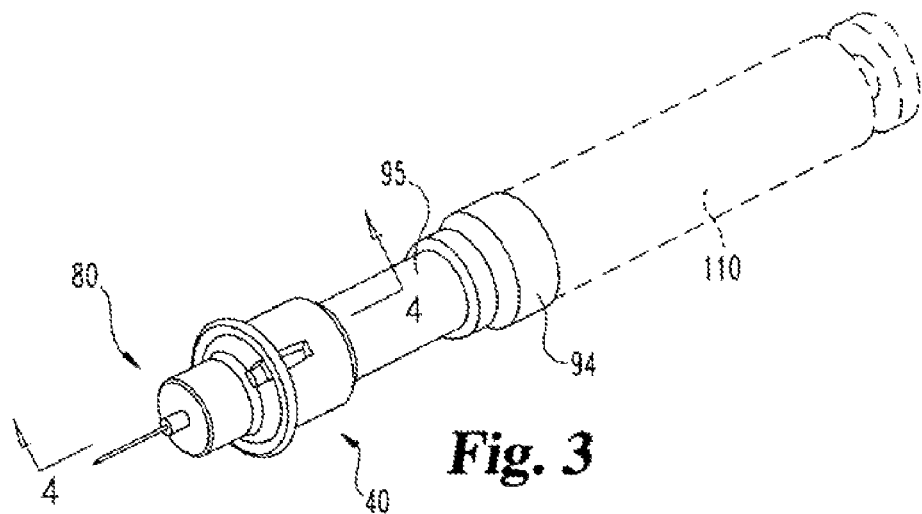
FIG. 3 is a perspective view of the components of FIG. 2 after assembly and attachment to an abstractly shown injection pen for use.

Fastening sleeve 94 includes an axial throughbore 93 in which is fixedly attached, such as with adhesives, press fit or snap/detent features, the rearward end of cartridge barrel portion 95. Fastening sleeve 94 includes means for being mountable to an injection device, such as an injection pen, that is operable to force the medication from the cartridge assembly 90. For example, the rearward end of sleeve 94 may be internally threaded to be removably screwable onto a reusable injection pen shown abstractly in FIG. 3 at 110, which injection pen has a not shown drive member insertable within the cartridge barrel so as to advance piston 102 when operated.

Pen needle 80 is of known construction and includes a double-ended needle cannula or injection needle 82 having a forward tip 84 at one end and a rearward tip 85 at the other. Injection needle 82 is mounted in a plastic, tubular hub 86 that is internally threaded at 87.

Figure 5:
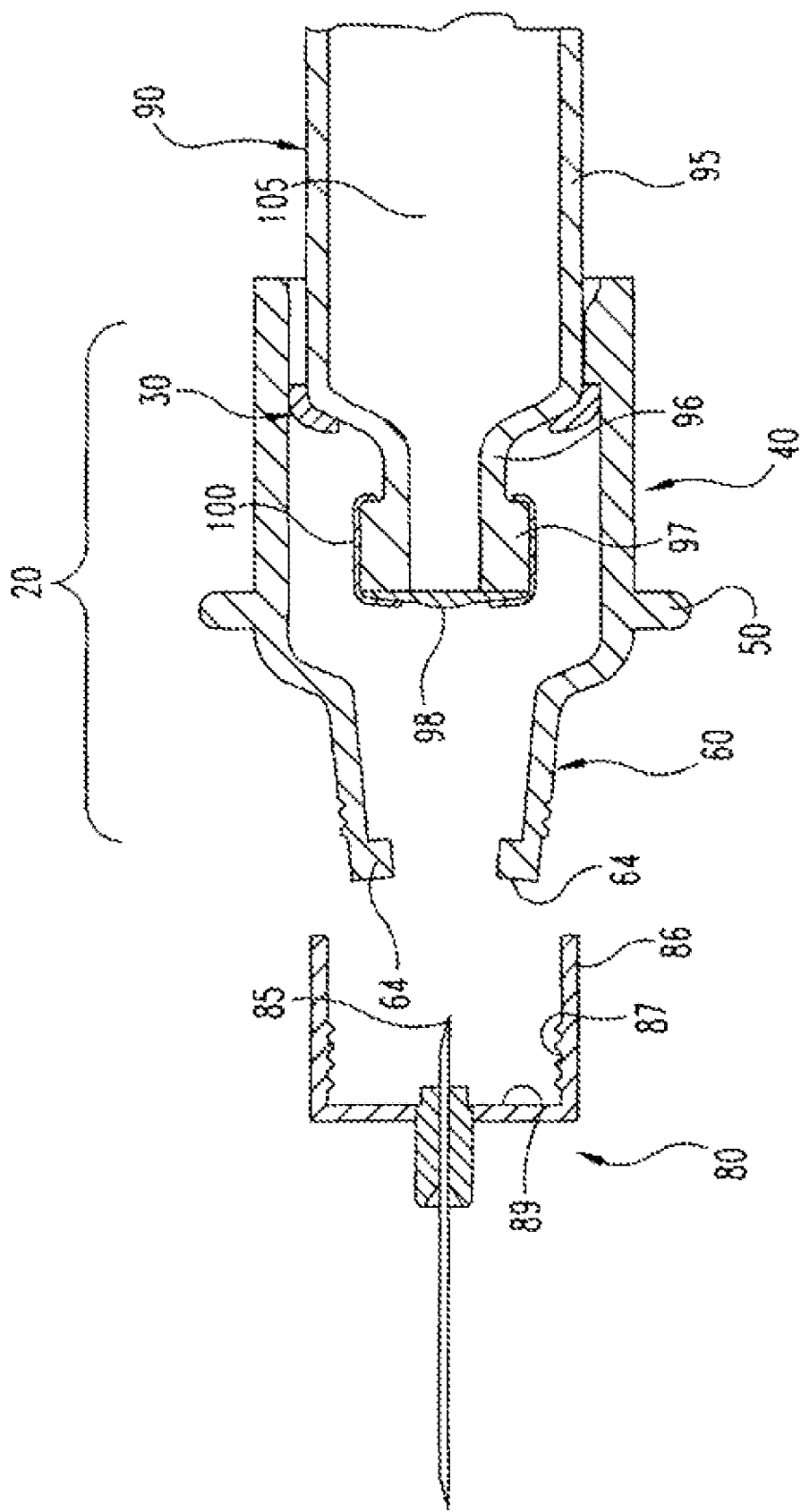
FIG. 5 is a longitudinal cross-sectional view of the components of FIG. 4 after the needle mounting assembly has been operated to remove the pen needle.

To use mounting assembly 20, it is arranged as shown in FIG. 5 with the collet 40 being in a forward state relative to the collar 30 and cartridge assembly 90, and with the pen needle 80 axially aligned therewith. A known cover of the needle tip 84 is not shown in the Figures but preferably will be used to limit accidental needle sticks when pen needle 80 is held by the user during this mounting process. In this mounting assembly arrangement, the fingers 60 are in a relaxed and radially collapsed position such that they will have a loose fit with the inside diameter of the needle hub when the aligned pen needle is moved axially to be placed thereover, in which loose fit the pen needle can be freely axially placed onto and freely axially removed from the fingers if desired. As pen needle 80 and mounting assembly 20 are manually brought axially together, a direct engagement of the underside 89 of hub 86 with the forward faces of lips 64 of the fingers forces collet 40 rearward. During this rearward movement of the pen needle relative to the cartridge assembly, in which needle tip 85 pierces septum 98 to extend into medication reservoir 105, the cammable surfaces 68 slide along crimp seal 100 such that fingers 60 radially expand inside the needle hub 86 to engage the threading 87. Movement of pen needle 80 and collet 40 is halted when, for example, the forward face of crimp seal 100 abuts the underside of lips 64 of fingers 60, at which time the mounting assembly 20 with mounted pen needle 80 are arranged in the ready to deliver medicine arrangement of FIG. 4.

To remove for disposal the pen needle 80 after use, the user grips collet 40 on sleeve 48 and moves it axially forward relative to the held cartridge assembly 90 until the forward faces of detents 51 abut collar 30 to halt the collet forward movement. Rib 50 may be pushed on forward by a user's digit to facilitate this forward movement, but pen needle 80 need not be touched. As collet 40 and its mounted pen needle are so moved forward, the needle tip 85 is withdrawn from the septum 98 and crimp seal 100 is in effect withdrawn axially from between fingers 60, allowing fingers 60 to relax back to their radially collapsed position at which needle hub threads 87 are disengaged and pen needle 80 can by gravity fall from a downward directed mounting assembly 20, such as into a sharps container or other disposal receptacle that is positioned below but not necessarily engaged with the pen needle. A replacement pen needle can then be mounted to assembly 20 as described above when needed.

Figure 6:
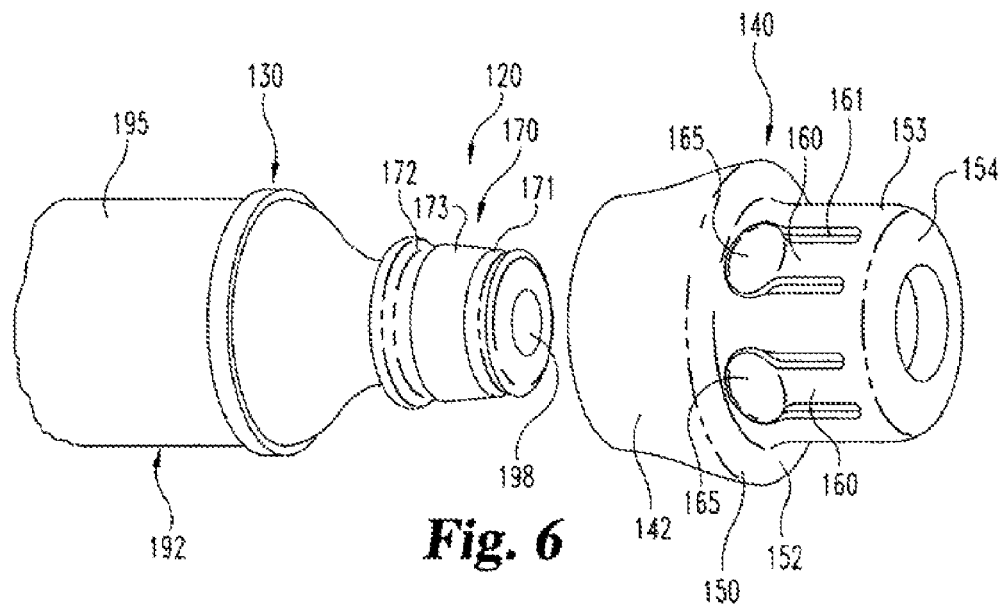
FIG. 6 is a front perspective view of a another embodiment of a needle mounting assembly of the present invention.
Figure 7:
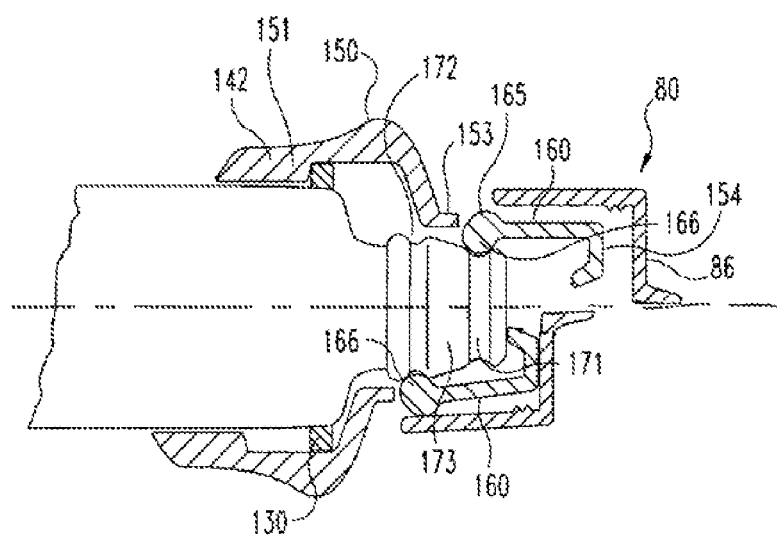
FIG. 7 is a diagrammatic, partial longitudinal cross-sectional view of the needle mounting assembly of FIG. 6 at different stages of its use.

Referring now to FIGS. 6 and 7, there is shown an alternate embodiment of a needle mounting assembly of the present invention. The needle mounting assembly, generally designated 120, includes a collar 130, a collet 140, and a complementary crimp seal 170.

Collar 130 has a ring-shape and is axially and rotatably secured to the barrel 195 of a cartridge 192. Cartridge 192 is identical to cartridge 92 except for the use of the crimp seal 170 instead of the crimp seal 100 to secure septum 198 to the cartridge body. Crimp seal 170 includes a first circumferential groove 171 and a second circumferential groove 172 that is axially positioned rearward of first groove 171. Between grooves 171 and 172, the outer radial periphery of crimp seal 170 slopes radially outward as it extends rearward to provide a ramping or camming surface 173.

Collet 140 includes a sleeve 142 with a flared radial periphery that forms a push surface 150. A tapering portion 152 of the sleeve forward of push surface 150 ends in a hollow cylindrical finger support 153 on which are disposed four axially extending fingers 160. The interior surface of sleeve 142 includes detents 151 for engaging the rear face of collar 130 to frustrate collet removal.

Fingers 160 are four in number and are defined by cutouts 161 in finger support 153. Each finger 160 is cantilevered with its forward end resiliently formed with support 153 and with the finger body axially extending rearward. At their rearward end, each finger includes a radially outwardly protruding boss 165 and a radially inwardly protruding boss 166.

Needle mounting assembly 120 may be used with the same pen needle 80 as shown with respect to the embodiment of FIG. 1, although the pen needle shown in FIG. 7 is shown without its cannula to facilitate illustration.

With reference to FIG. 7, pen needle 80 may be mounted via assembly 120 by aligning the needle hub over the forward end of finger support 153 as abstractly shown in the top half of FIG. 7. Initially, collet 140 is in the position shown in the top half of FIG. 7 due to bosses 166 seating within crimp seal groove 171, with the fingers 160 extending forward of the crimp seal. When pen needle 80 is moved toward collet 140, the underside of hub 86 abuts the forward annular face 154 of finger support 153, and further forcible pen needle shifting drives collet 140 rearward relative to the cartridge 192. The axial force applied must be sufficient to overcome the resistance to bending of fingers 160, as fingers 160 must be splayed outward by the unseating of bosses 166 from groove 171 and the sliding of the bosses along ramped surface 173, until the fingers snap back in partially when the bosses 166 reach and seat within groove 172, at which point rearward movement of the collet 140 is halted. During this splaying outward of fingers 160, the bosses 165 are brought into contact with the interior surface of hub 86, and such bosses 165 remain in frictional engagement therewith after bosses 166 seat in the rearward groove 172. At this axial position of the collet, which is shown in the bottom half of FIG. 7, the pen needle 80 is mounted in fluid communication with the cartridge 192 and ready for use.

To remove pen needle 80, sleeve 142 can be manually gripped and advanced relative to cartridge 195 such that finger bosses 166 slide up and out of the rearward groove 172 and forward along camming surface 173 until seated in forward groove 171, at which point further forward movement of collar 140 is prevented by the engagement of detents 151 with the rearward face of collar 130, and at which point the pen needle 80 can be axially removed by gravity as bosses 165 no longer frustrate needle removal.

Figure 8:
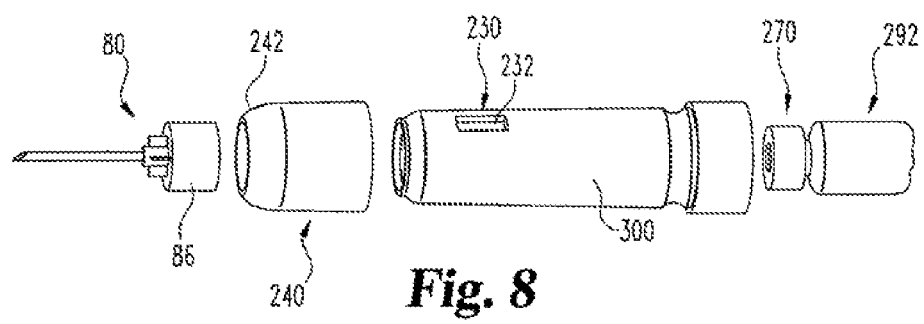
FIG. 8 is a perspective view in exploded form another needle mounting assembly of the present invention with a pen needle and cartridge.
Figure 9:
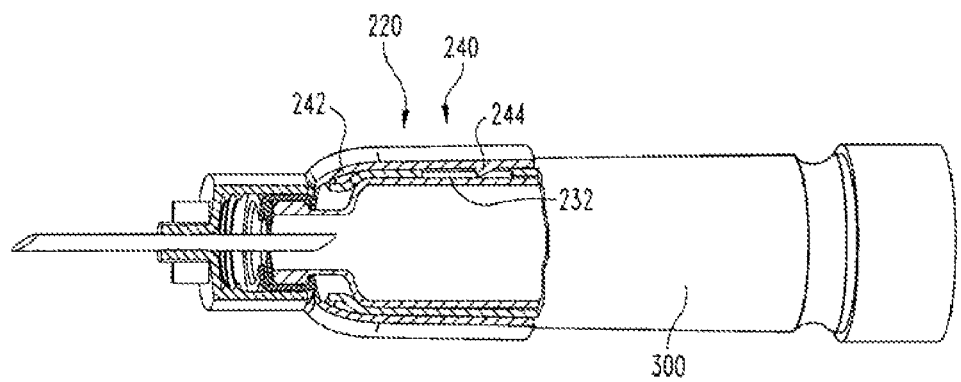
FIG. 9 is a perspective view in partial longitudinal cross-section of the elements of FIG. 8 when assembled and with the pen needle operationally mounted.

Referring now to FIGS. 8 and 9, there is shown still another alternate embodiment of a needle mounting assembly of the present invention. The needle mounting assembly, generally designated 220, includes a collar 230, a collet 240, and a crimp seal 270.

Collar 230 is formed as recesses or longitudinal slots 232 within a tubular cartridge retainer 300 that is mounted to a not shown dosing assembly of an injection pen. The cartridge 292 is identical to cartridge 92 except for the use of crimp seal 270 that is sized and shaped to frictionally engage the interior of a standard pen needle hub. Crimp seal 270 fits completely through the open forward end of retainer 300.

Collet 240 is formed as a tapering sleeve with a reduced diameter forward end 242 that has a central opening with a larger diameter than that of crimp seal 270, but that has a smaller diameter than that of the hub 86 of the standard pen needle 80. The interior surface of the collet sleeve includes detents 244 that axially slide within slots 232. A not shown, small detent on the sleeve interior may fit within a not shown indent on the retainer exterior periphery to hold the collet in the rearward, ready-for-needle-mounting position shown in FIG. 9.

When a standard pen needle 80 is frictionally mounted to crimp seal 270 by being axially pushed thereon, the device with mounting assembly 220 may be used in a conventional fashion. To remove pen needle 80 from the arrangement shown in FIG. 9, collet 240 is gripped and simply manually shifted forward along retainer 300, during which time the forward end 242 abuts the rear edge of the needle hub 86 and forces the pen needle hub out of its frictional engagement with crimp seal 270 to remove pen needle 80 from the assembly. The forward movement of collet 240 on the retainer 300 is halted when the transverse forward face of detents 244 abut the forward end of the slots 232. In an alternate embodiment, a spring may be provided to bias the collet 240 to its rearward position.

While this invention has been shown and described as having preferred designs, the present invention may be modified within the spirit and scope of this disclosure. For example, a design in which the resilient fingers of a collet are splayed outward in a relaxed state, but which fingers are held radially in by engagement with another feature of the assembly when the collet is in a forward position to allow the pen needle hub to fit therearound, may be provided. This application is therefore intended to cover any variations, uses or adaptations of the invention using its general principles. Further, this application is intended to cover such departures from the present disclosure as come within known or customary practice in the art to which this invention pertains.

We claim:

1. A needle mounting assembly for mounting a pen needle in fluid communication with a medication cartridge including an outlet end with a septum, the needle mounting assembly comprising:

a collet defining an opening in which is slidably fittable the outlet end of the cartridge, said collet shiftable relative to the cartridge outlet end between a first axial position and a second axial position, said collet including a base and a plurality of fingers that are forward of said base;

a stop collar disposed at a fixed axial location on one of the cartridge and a retainer for the cartridge, said stop collar adapted to halt movement of said collet at said first axial position when said collet moves from said second axial position;

wherein when said collet is disposed in said first axial position, said plurality of fingers extend forward of the cartridge outlet end and are disposed in a first radial arrangement in which a needle hub of the pen needle can be freely axially placed onto and freely axially removed from the plurality of fingers;

wherein when said collet is moved to said second position from said first position when the needle hub is freely placed onto the plurality of fingers, said plurality of fingers are shifted by engagement with the cartridge outlet end to a second radial arrangement to operationally secure the needle hub for medication delivery with a tip of a cannula of the pen needle piercing the cartridge septum;

wherein when said collet at said second position with the needle hub operationally secured by said plurality of fingers is moved to said first position, the tip of the cannula of the pen needle is withdrawn from the cartridge septum and said plurality of fingers shift back to said first radial arrangement for free axial removal of the needle hub from the mounting assembly; and wherein each of said plurality of fingers includes an outer radial periphery for engagement with an internal threading of the needle hub.

2. The needle mounting assembly of claim 1 wherein each outer radial periphery includes partial threads for engagement with the internal threading of the needle hub.

3. The needle mounting assembly of claim 1 wherein each of said plurality of fingers includes a radially inward surface that is cammed radially outward by direct engagement with a septum securing crimp seal of the cartridge outlet end to achieve said plurality of fingers being shifted by engagement with the cartridge outlet end.

4. The needle mounting assembly of claim 1 wherein said collet base includes a manually grippable sleeve with at least one detent on an interior sleeve surface which is sized and shaped to abut said stop collar to halt movement of said collet at said first axial position when said collet moves from said second axial position.

5. The needle mounting assembly of claim 1 wherein said collet base includes a circumferential rib that protrudes radially outward from said sleeve to serve as a digit abutment surface, said rib disposed at a forward region of said sleeve and rearward of said plurality of fingers.

6. The needle mounting assembly of claim 1 wherein said stop collar is axially secured to the cartridge.

7. The needle mounting assembly of claim 1 wherein said plurality of resilient fingers comprises four equally angularly spaced fingers that axially project forward from said base and in a forward direction tilt radially inward.

* * * * *

UNITED STATES PATENT AND TRADEMARK OFFICE
CERTIFICATE OF CORRECTION

| | | |
|---|---|---|
| PATENT NO. | : 7,988,678 B2 | Page 1 of 1 |
| APPLICATION NO. | : 12/307702 | |
| DATED | : August 2, 2011 | |
| INVENTOR(S) | : Rodney Hal Monson et al. | |

It is certified that error appears in the above-identified patent and that said Letters Patent is hereby corrected as shown below:

In Column 8, line 31, which is in Claim 7, delete "resilient".

Signed and Sealed this
Fourteenth Day of February, 2012

David J. Kappos
*Director of the United States Patent and Trademark Office*